US00PP07805P

United States Patent [19]

Fleming

[11] Patent Number: Plant 7,805

[45] Date of Patent: Feb. 25, 1992

[54] KALANCHOE PLANT NAMED BEACON

[75] Inventor: Margaret M. Fleming, Soquel, Calif.

[73] Assignee: The Plant Company, Soquel, Calif.

[21] Appl. No.: 606,302

[22] Filed: Oct. 31, 1990

[51] Int. Cl.[5] ..... A01H 5/00
[52] U.S. Cl. ..... Plt./68
[58] Field of Search ..... Plt./68

*Primary Examiner*—James R. Feyrer
*Attorney, Agent, or Firm*—Foley & Lardner

[57] ABSTRACT

A Kalanchoe plant named Beacon particularly characterized by its yellow flower color, maturing to yellow gold; flower diameter of up to 16 mm at maturity; flowering response, from 11 weeks in summer to 13 weeks in winter after start of short days; floriferous, with excellent display of many flowers; good keeping quality of both flowers and foliage; excellent free branching with or without pinching; compact plant habit; responsiveness to B-9 to reduce internode length and peduncle elongation; and adaptability to various pot sizes.

2 Drawing Sheets

The present invention relates to a new and distinctive cultivar of Kalanchoe plant, botanically known as *Kalanchoe blossfeldiana* Poelln., and referred to by the cultivar name Beacon.

Beacon, identified as 579-369, is a product of a planned breeding program which had the objective of creating new Kalanchoe cultivars for year-round commercial production having an earlier flowering response, good branching yet compact flowering plants, suitability for flowering in pots ranging from 10 to 15 cm, and having good flower and foliage keeping quality.

Beacon was originated by the inventor Margaret M. Fleming from a controlled selfing of the parent plant, an unnamed seedling identified as 402-087, in Half Moon Bay, Calif., in 1984. The parent 402-087 was the result of a cross between Cinnabar, disclosed in U.S. Plant Pat. No. 5,160, and Fortyniner, disclosed in U.S. Plant Pat. No. 5,256.

Beacon was discovered and selected as one flowering plant within the progeny of the stated selfing by Margaret M. Fleming in February of 1986 in a controlled environment in Soquel, Calif.

The first act of asexual reproduction of Beacon was accomplished when vegetative cuttings were taken from the initial selection in July 1986 in a controlled environment in Soquel, Calif., by Margaret M. Fleming.

Horticultural examination of controlled flowerings of successive plantings has shown that the unique combination of characteristics as herein disclosed for Beacon are firmly fixed and are retained through successive generations of asexual reproduction. Beacon has not been observed under all possible environmental conditions. The phenotype may vary significantly with variations in environment such as temperature, light intensity and day length.

The following observations, measurements and comparisons describe plants grown in Soquel, Calif., under greenhouse conditions which approximate those generally used in commercial greenhouse practice.

The following traits have been repeatedly observed and are determined to be basic characteristics of Beacon, which, in combination, distinguish this Kalanchoe as a new and distinct cultivar:

1. Yellow flower color, maturing to yellow-gold.
2. Flower diameter of 14 to 16 mm at maturity.

3. Flowering response of from 11 weeks in summer to 13 weeks in winter after start of short days.
4. Floriferous, with excellent display of many flowers.
5. Excellent keeping quality of both flowers and foliage, with each floret lasting two weeks or more under normal conditions of finishing and holding.
6. Branches freely with or without pinching.
7. Medium plant habit.
8. Responsiveness to B-9 to reduce internode length and peduncle elongation.
9. Proper scheduling makes this new cultivar suitable for production in 10 cm to 15 cm pots.

The accompanying colored photographic drawings show typical inflorescence and leaf characteristics of Beacon, with colors being as nearly ture as possible with illustrations of this type.

Sheet 1 is a color ph0tograph of Beacon grown as a non-pinched flowering kalanchoe in a 10 cm pot.

Sheet 2 is a black and white photograph showing the leaves of Beacon at three stages of development (mature, intermediate and immature).

Of the commercial cultivars known to the inventor, the most similar in comparison to Beacon is the grandparent cultivar Fortyniner. In comparison to Fortyniner, Beacon has a more yellow flower color, a larger flower diameter, a better display of more flowers, and markedly improved keeping quality of flowers and foliage. Similar traits are flowering response, free branching, medium plant habit, responsiveness to B-9, and adaptability to various pot sizes.

Beacon can also be compared to Cinnabar, the female grandparent. The flower color of Beacon is pure yellow, compared to the red/orange flower color of Cinnabar. The flower diameter of 14-16 mm for Beacon is slightly less than the flower diameter of Cinnabar. Also, the flowering response of Beacon is approximately two weeks later than Cinnabar, when both cultivars are grown under the same conditions. However, the flowers of Beacon are long keeping, in excess of two weeks. This is sharply contrasted with the flowers of Cinnabar, which normally fade in approximately 7-10 days.

In the following description color references are made to The Royal Horticultural Society Colour Chart. The color values were determined on plant material grown as a non-pinched pot plant in a 10 cm pot in Soquel, Calif., on Aug. 9, 1988.

Classification:

*Botanical.*—*Kalanchoe blossfeldiana* Poelln. cv. Beacon.

*Commercial.*—Flowering pot Kalanchoe.

Parentage: Controlled selfing of an unnamed seedling, 402-087.

Propagation:

(A) *Type cutting.*—Short tip cutting, with stems up to 2 cm.

(B) *Time to root.*—10 days at 21° C. in summer; 14 days at 21° C. in winter.

(C) *Rooting habit.*—Many very fine roots, fibrous.

Plant Description:

(A) *Form.*—Medium, compact, upright growth. Growing and scheduling practices can produce a small plant in a 10 cm pot up to a larger plant in a 15 cm pot.

(B) *Habit of growth.*—Rate of growth moderate to vigorous for this type of plant. Generally, shoots are formed at every node, with internodes being 12-25 mm for a vegetative natural plant; height of plant above 10 cm pot approximately 15-25 cm, based on 2-3 applications of 3500 ppm B-9 SP growth regulator.

(c) *Foliage description.*—Leaves simple, opposite, slightly lobed. 1. Size: Average full grown leaf in a 10 cm flowering pot is 145 mm long×85 mm wide. 2. Shape: Ovate to elliptic, apex obtuse, base attenuate. 3. Texture: Glabrous, coriaceous, succulent. 4. Margin: Sinuate to crenate. 5. Color (mature foliage: Upper surface 147A; under surface 147B. Under certain conditions tips and margins of mature foliage on both upper and under surface are slightly streaked with 183A to 183C. 6. Durability: Excellent; no degradation observed even on the lower foliage of plants retained for months beyond normal life expectancy. Yellow flowered varieties normally may be expected to have poor lower foliage — with Beacon this does not follow. 7. Foliar diseases: Resistant or immune to Powdery Mildew. Chlorosis, necrotic spots, tip die-back, stem rot and root rot have not been observed.

Flowering Description:

(A) *Flowering habit.*—Inflorescence of each shoot is formed by dichotomous branching, starting with opening of terminal flower of main axis, followed by terminal flowers of the side branches, continuing with subsequent development of branches in the inflorescence. Opening of new buds (12-17 mm) will continue for two months or more. Individual flowers last two weeks or more after opening. No perceived fragrance.

(B) *Flowering response.*—Flowering time under controlled day length after start of short days is 11 weeks in summer to 13 weeks in winter.

(C) *Flowers borne.*—Compound dichasial cymes; peduncle length 5-13 cm, diameter 4-8 mm; pedicel length 5-7 mm, diameter greater than 1 mm.

(D) *Quantity of flowers.*—Very floriferous; floret count 80-100 per primary inflorescence; 400-500 total per 10 cm pot plant, commercial culture.

(E) *Petals.*—1. Shape: Slightly pointed to almost round. 2. Color: Upper surface: 10A to 10B, maturing to 15D. Under surface: 10C to 10D, maturing to 13D. 3. Number of petals: 4, united in corolla. 4. Flower diameter: 14 to 16 mm at maturity.

(F) *Reproductive organs.*—1. Stamens: 8 in number. a. Anther shape: Flat, elliptical, color yellow. b. Filament color: Light green. c. Pollen color: Yellow. 2. Pistils: a. Stigma shape: Flat, crystalline, color greenish white. b. Style color: Light green. c. Ovaries: 4-celled, color light green.

(G) *Flower diseases.*—None noted to date; resistant to Botrytis; no problems with color breaking or excess fading.

I claim:

1. A new and distinct Kalanchoe plant named Beacon, as described and illustrated.

* * * * *

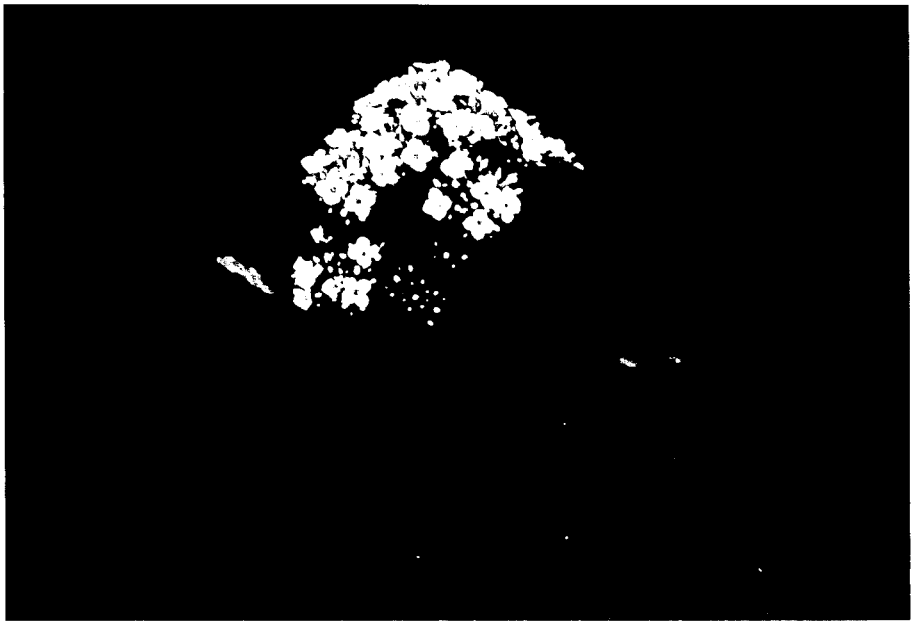

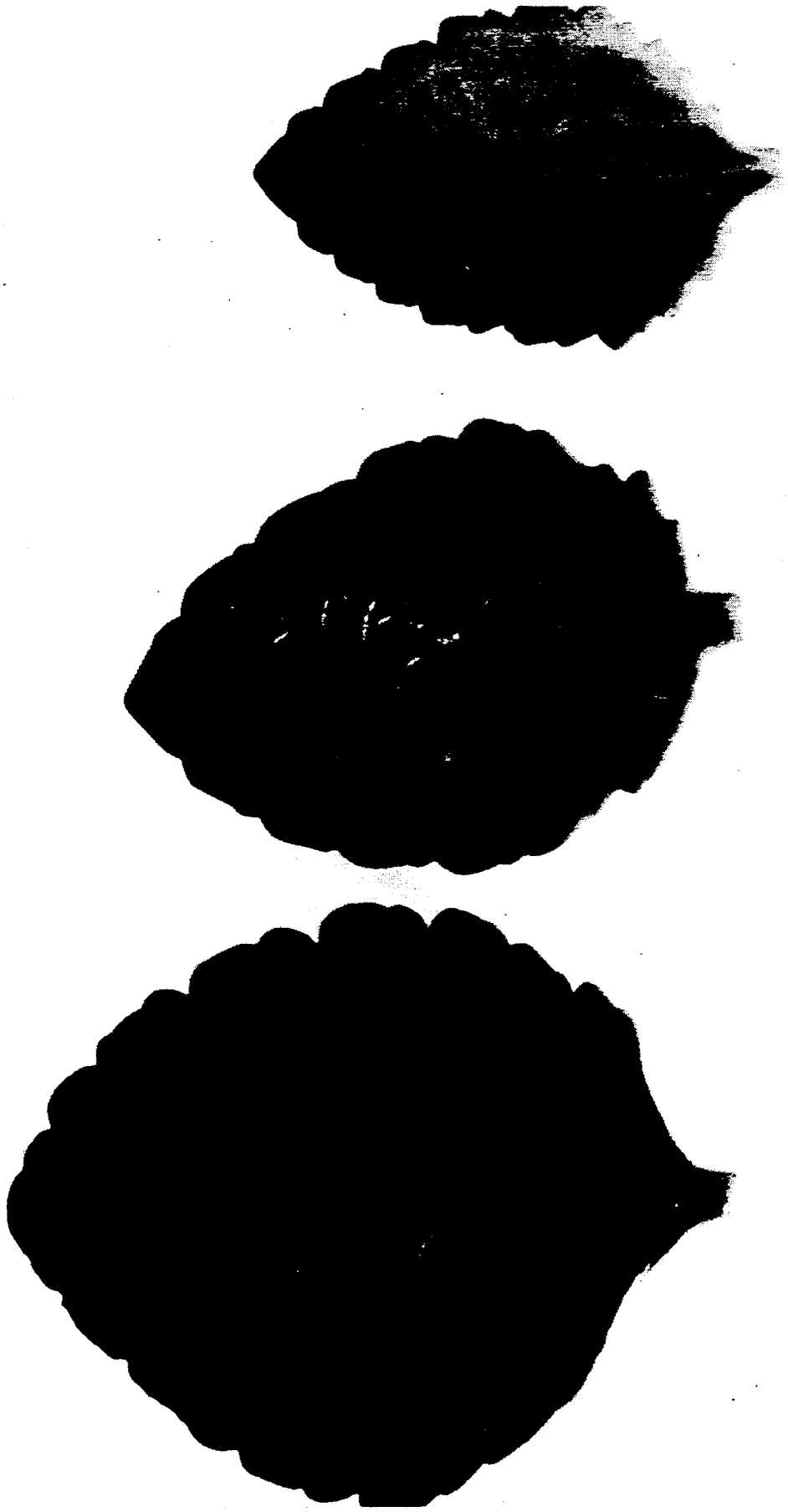
BEACON